US008992428B2

(12) United States Patent
Palti

(10) Patent No.: US 8,992,428 B2
(45) Date of Patent: *Mar. 31, 2015

(54) TRANSTHORACIC CARDIO-PULMONARY MONITOR

(75) Inventor: Yoram Palti, Haifa (IL)

(73) Assignee: Echosense Inc., Road Town, Tortola (BV)

(*) Notice: Subject to any disclaimer, the term of this patent is extended or adjusted under 35 U.S.C. 154(b) by 174 days.

This patent is subject to a terminal disclaimer.

(21) Appl. No.: 13/364,851

(22) Filed: Feb. 2, 2012

(65) Prior Publication Data
US 2012/0197128 A1 Aug. 2, 2012

Related U.S. Application Data

(63) Continuation-in-part of application No. 12/912,988, filed on Oct. 27, 2010.

(60) Provisional application No. 61/439,213, filed on Feb. 3, 2011, provisional application No. 61/255,322, filed on Oct. 27, 2009, provisional application No. 61/326,133, filed on Apr. 20, 2010, provisional application No. 61/405,454, filed on Oct. 21, 2010.

(51) Int. Cl.
A61B 8/00 (2006.01)
A61B 8/02 (2006.01)
(Continued)

(52) U.S. Cl.
CPC ............... A61B 8/02 (2013.01); A61B 5/0816 (2013.01); A61B 8/06 (2013.01); A61B 8/0883 (2013.01); A61B 8/488 (2013.01); A61B 8/5223 (2013.01); A61B 8/543 (2013.01)
USPC ........... 600/453; 600/437; 600/455; 600/457

(58) Field of Classification Search
None
See application file for complete search history.

(56) References Cited

U.S. PATENT DOCUMENTS 5,038,771 A * 8/1991 Dietz .................. 128/204.21
5,507,291 A 4/1996 Stirbl et al.
(Continued)

FOREIGN PATENT DOCUMENTS

EP 0 573 249 12/1993
EP 1 726 262 11/2006
(Continued)

OTHER PUBLICATIONS

Laudy et al. "Doppler ultrasound imaging: a new technique to detect lung hypoplasia before birth?", Ultrasound Obstet. Gynecol. (1996), pp. 189-192.*
(Continued)

Primary Examiner — Long V Le
Assistant Examiner — Farshad Negarestan
(74) Attorney, Agent, or Firm — Proskauer

(57) ABSTRACT

Operation of a patient's heart or lungs may be analyzed by transmitting ultrasound energy into the patient's lung, and detecting Doppler shifts of reflected ultrasound induced by moving borders between blood vessels/soft tissue in the lung and air filled alveoli that surround the blood vessels. Movement of the border is caused by pressure waves in the blood vessels that result in changes in diameter of those blood vessels. The detected Doppler shifts are processed with a noise reduction algorithm, and periodic features in the resulting data are then analyzed to determine the rate of the patient's heartbeat, the rate of the patient's breathing, and/or the appearance of anomalies in the patient's heartbeat.

26 Claims, 15 Drawing Sheets

(51) Int. Cl.
*A61B 5/08* (2006.01)
*A61B 8/06* (2006.01)
*A61B 8/08* (2006.01)

(56) References Cited

U.S. PATENT DOCUMENTS

| | | |
|---|---|---|
| 6,050,948 A | 4/2000 | Sasaki et al. |
| 6,293,913 B1 | 9/2001 | Tsujino et al. |
| 2005/0215904 A1 | 9/2005 | Sumanaweera et al. |
| 2007/0165872 A1 | 7/2007 | Bridger et al. |
| 2008/0039725 A1 | 2/2008 | Man et al. |
| 2009/0318777 A1 | 12/2009 | Kameyama |
| 2010/0137717 A1* | 6/2010 | Strand ............................ 600/454 |

FOREIGN PATENT DOCUMENTS

| | | |
|---|---|---|
| FR | 2 944 199 | 10/2010 |
| WO | 2006096915 | 9/2006 |
| WO | 2007107926 | 9/2007 |

OTHER PUBLICATIONS

McHugh R et al; "An Ultrasonic Pulsed Doppler Instrument for Monitoring Human Fetal Breathing in Utero", Ultrasound in Medicine and Biology, New York, NY, vol. 3, No. 4, Jan. 1, 1978, pp. 381-384, XP026409492.

Greenspan H et al.; "Doppler echocardiography flow-velocity image analysis for patients with atrial fibrillation", Ultrasound in Medicine and Biology, New York, NY, vol. 31, No. 8, Aug. 1, 2005, pp. 1031-1040, XP027605609.

Search Report and Written Opinion from corresponding application PCT/IB2012/000180.

* cited by examiner

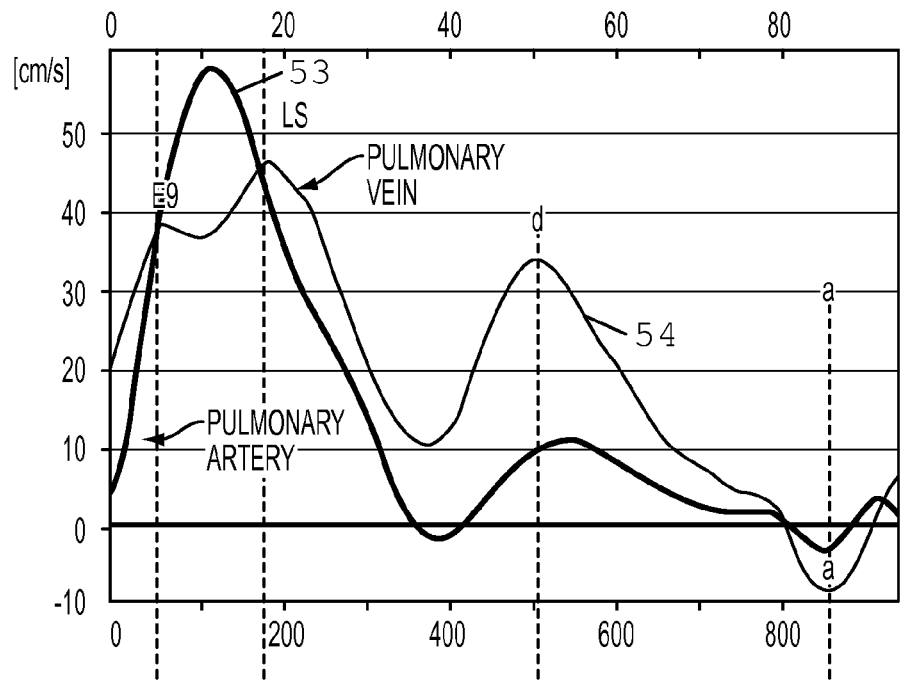
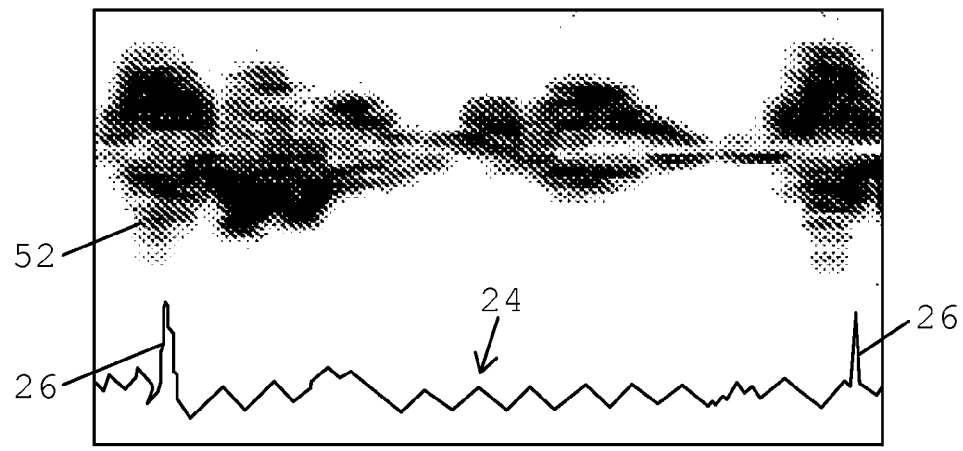
FIG. 5A

TRANSTHORACIC CARDIO-PULMONARY MONITOR

CROSS REFERENCE TO RELATED APPLICATIONS

This Application claims the benefit of U.S. Provisional Application 61/439,213 (filed Feb. 3, 2011); and this application is also a continuation-in-part of U.S. application Ser. No. 12/912,988 (filed Oct. 27, 2010), which claims the benefit of U.S. Provisional Application 61/255,322 (filed Oct. 27, 2009), U.S. Provisional Application 61/326,133 (filed Apr. 20, 2010), and U.S. Provisional Application 61/405,454 (filed Oct. 21, 2010). Each of the applications identified above is incorporated herein by reference.

BACKGROUND

Patients in unstable or critical medical condition often require continuous vital sign monitoring. This includes hospitalized patients in ICUs, internal medicine, cardiology, surgery, etc. Similarly, patients in nursing homes or their own home may need to be monitored. The data gathered by the monitoring system is often relayed to a local display and analysis, remote display and analysis (in locations such as a nursing home, a telemedicine center, etc). Various alarms may also be activated by the data which may be analyzed on-line or off-line.

In practice, in the non-ICU environment, the main parameter monitored is the ECG, often with the addition of respiration, blood oxygen saturation level, and blood pressure. However, the information that these parameters provide regarding the clinical state of the patient is limited, and the patient may fall into a dangerously critical situation without the monitor providing in a sufficiently early time reliable warning signs or alarms. This failure may be due to the fact that the information provided by the ECG is mainly related to arrhythmias and in some cases to significant cardiac ischemia, and the information provided by the $O_2$ saturation is also limited to severe cardio-pulmonary failure. As a result, other dangerous conditions may go undetected.

SUMMARY OF THE INVENTION

One aspect of the invention relates to a method of determining a breathing rate of a patient. This method includes the steps of obtaining, using an ultrasound probe that is aimed at the patient's lung, Doppler ultrasound power and velocity data for a period of time that corresponds to a plurality of cardiac cycles. The power and velocity data obtained in the obtaining step are processed using at least one noise reduction algorithm. An envelope of the power and velocity data with respect to time is then extracted, wherein at least one parameter used in the envelope extraction is selected to track variations that correspond to an expected breathing cycle. A periodic feature of the extracted envelope is identified and timing of the identified periodic feature is determined. An indication of the breathing rate is then output based on the determined timing. In some embodiments, the at least one parameter is configured to pass frequencies less than 0.25 Hz and attenuate frequencies greater than 1.5 Hz.

Another aspect of the invention relates to an apparatus for determining a breathing rate of a patient. This apparatus includes an ultrasound-frequency signal generator configured to drive an ultrasound transducer and a receiver configured to receive ultrasound-frequency return signals reflected from a target region in the patient's lungs and detect Doppler shifts of the return signals. It also includes a processor configured to (a) process the detected Doppler shifts with a noise reduction algorithm and output processed power and velocity data for a period of time that corresponds to a plurality of cardiac cycles, (b) extract an envelope of the power and velocity data with respect to time, wherein at least one parameter used for the envelope extraction is selected to track variations that correspond to an expected breathing cycle, (c) identify a periodic feature of the extracted envelope, (d) determine timing of the identified periodic feature, and (e) output an indication of the breathing rate based on the determined timing. The apparatus is configured for use together with an ultrasound probe that includes the ultrasound transducer.

Another aspect of the invention relates to a method of monitoring a patient's heart. This method includes the steps of obtaining, using an ultrasound probe that is aimed at the patient's lung, Doppler ultrasound power and velocity data for a period of time that corresponds to a plurality of cardiac cycles. The power and velocity data obtained in the obtaining step are processed using at least one noise reduction algorithm and features in the power and velocity data that occur once per cardiac cycle are identified. Timing between the identified features is then determined.

The identified features may optionally be at least one of (a) a feature that corresponds to systolic ventricular contraction, (b) a feature that corresponds to ventricular relaxation, (c) a feature that corresponds to a diastolic rapid filling phase, (d) a feature that corresponds to diastasis, and (e) a feature that corresponds to atrial contraction.

Some embodiments include an additional step of outputting an indication of how fast the patient's heart is beating based on the timing determined in the determining step. Other embodiments include the additional steps of predicting a time when a particular feature is expected based on past occurrences of identified features, detecting a presence of the particular feature at a time that was not predicted in the predicting step, and outputting an indication that the particular feature was detected at an unpredicted time.

Another aspect of the invention relates to an apparatus for monitoring a patient's heart. This apparatus includes an ultrasound-frequency signal generator configured to drive an ultrasound transducer and a receiver configured to receive ultrasound-frequency return signals reflected from a target region in the patient's lungs and detect Doppler shifts of the return signals. It also includes a processor configured to (a) process the detected Doppler shifts with a noise reduction algorithm and output processed power and velocity data for a period of time that corresponds to a plurality of cardiac cycles, (b) identify features in the power and velocity data that occur once per cardiac cycle, and (c) determine timing between the identified features.

In some embodiments, the processor is further configured output an indication of how fast the patient's heart is beating based on the determined timing. In other embodiments, the processor is further configured to predict a time when a particular feature is expected based on past occurrences of identified features, detect a presence of the particular feature at a time that was not predicted, and output an indication that the particular feature was detected at an unpredicted time.

BRIEF DESCRIPTION OF THE DRAWINGS

FIG. 5A compares a TPD output of a normal subject with tracings of blood flow velocity in a pulmonary artery and vein.

FIGS. 13C and 13D depict the power in various features corresponding to

FIGS. 13A and 13B, respectively.

DESCRIPTION OF THE PREFERRED EMBODIMENTS

The inventors have recognized that the pulmonary circulation and the pulmonary ultrasound scattering properties may be significantly modified in a large variety of cardio-pulmonary patho-physiological conditions and diseases, and that such information may be of significant diagnostic and therapeutic importance. The embodiments described herein are designed to monitor the functionality of the arteries and veins in the lungs, as well as the integrity and functionality of the lung tissues that surround them, using Doppler ultrasound. It is referred to herein as "Transthoracic Pulmonary Doppler" or "TPD".

Figure 1:
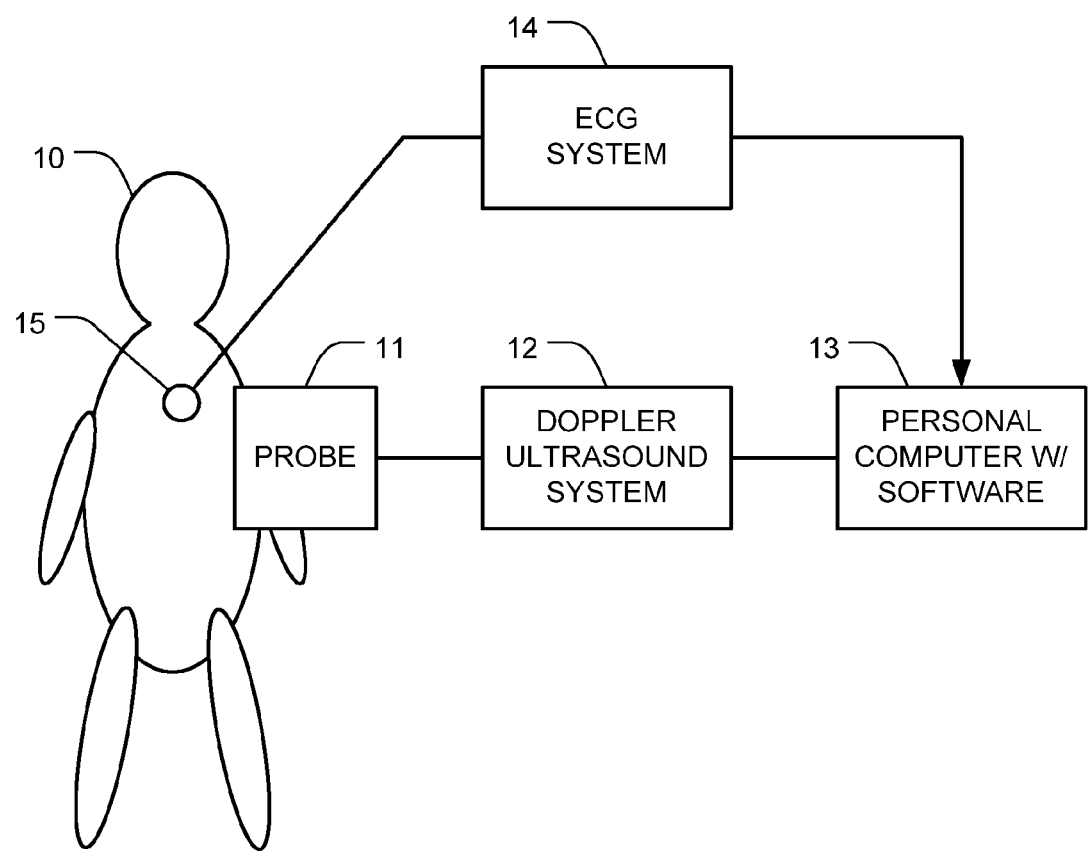
FIG. 1 is a block diagram of an embodiment of a Transthoracic Pulmonary Doppler ("TPD") System.

FIG. 1 is a block diagram of one such embodiment. A Doppler ultrasound machine 12 in conjunction with the probe 11 (which includes an ultrasound transducer) is used to determine the power at every relevant velocity in a target region of the subject 10, over time, in a conventional manner. This may be accomplished by generating pulsed ultrasound beams, picking up the reflected energy, calculating the Doppler shifts, and processing the data thus obtained to provide the matrix of power and corresponding velocities of the ultrasound reflectors. One example of a suitable Doppler ultrasound machine 12 is the Sonara/tek pulsed Trans-Cranial-Doppler device (available from Viasys, Madison, Wis., US), which is a pulsed Doppler system. The Doppler ultrasound machine 12 sends the data that it captures to a personal computer 13 that is loaded with software to generate a conventional Doppler ultrasound display (e.g., on a monitor associated with the computer 13) in which the x axis represents time, the y axis represents velocity, and power is represented by color. Suitable software for controlling the ultrasound parameters is also available from Viasys. Note that in alternative embodiments, the functions of the Doppler ultrasound machine 12 and personal computer 13 may be combined into a single device.

Preferably, an ECG system 14 is also provided. The ECG system 14 interfaces with conventional ECG leads 15 and generates an output in any conventional manner. The output is preferably synchronized in time with the Doppler ultrasound machine 12 so that both an ECG and ultrasound display can be displayed on the same time scale. The output of the ECG system 14 is provided to the personal computer 13 in any conventional manner. In alternative embodiments, it may be combined by the Doppler ultrasound machine 12 instead.

A standard TCD probe such as a 21 mm diameter, 2 MHz sensor with a focal length of 4 cm may be used as the probe 11. Suitable probes are available from Viasys for use with their Sonara/tek machines. Conventional probes for making Doppler ultrasound measurements of peripheral or cardiac blood vessels may also be used. These applications, however, typically use narrow beams, often shaped using a phased array transducer, to provide a high spatial resolution that is helpful for making geometrical characterization of the relatively small targets. While these narrow beams can produce usable results in the context of TPD, some preferred alternative embodiments use relatively wide beams, for example beams with an effective cross section of at least ¼ cm$^2$ (e.g., between ¼ and 3 cm$^2$). This may be accomplished by using a smaller transducer, and by using single element transducers instead of phased array transducers that are popular in other anatomical applications. In alternative embodiments, transducers with a relatively small number of elements (e.g., 4-6) can be used. Coin-shaped ultrasound Doppler probes (e.g., about 2 cm in diameter) are suitable for this application. When a wider beam is used, the system can take advantage of the fact that the lungs contain relatively large complexes of unspecified geometrical shape consisting of blood vessels (both arteries and veins) and their surrounding lung tissues.

Note that since imaging the lung with ultrasound is impossible because of the scattering, one has to scan for targets without guidelines, except for the known anatomy. Note also that scattering lowers the advantage of scanning by either phase array or by mechanical means. Furthermore, since the whole lung depth induces scattering, CW (continuous wave) ultrasound is less effective than PW (pulsed wave) Doppler ultrasound for pulmonary applications. Therefore, some preferred embodiments utilize PW ultrasound with relatively wide beams. Optionally, such embodiments may employ multiple sensors positioned on the surface of the body.

Optionally, specially selected or designed ultrasound probes and/or suitable beam power control may be used, including dynamic adjustable beam shape and size so as to enable measurement from variable tissue volumes. Note that in contrast to when Doppler is used for other tissue targets, here the average and integral of signals originating from relatively large volumes contain valuable information.

In addition to the standard software for generating a display from the Doppler signals, the personal computer 13 preferably includes software for activating the TPD and selecting the desired operating mode, display mode, and storage modes. The personal computer 13 also includes or has access to appropriate data storage resources (e.g., local or remote hard drives). The personal computer 13 preferably processes the original velocity-and-power vs. time data using one or more noise reduction (NR) algorithms that are optimized to minimize the noise created by the signal scattering and attenuation by the lung tissue.

One preferred approach to noise reduction involves two phases—averaging and edge detection. In the first phase, an averaged signal from a number of cardiac cycles is obtained by averaging the power/velocity data of N characteristic signals, where each of the N signals preferably represents a single cardiac cycle. N is preferably an integer between 4 and 20 (e.g., 10). Preferably, each signal is bounded by an R-wave at each end, although in alternative embodiments other points on the cardiac cycle may be used as a time reference point. The calculated averaged signal is assumed to characterize the spectrogram behavior for the subject, and therefore is the basis on which the relevant features are later determined. Note that while it is preferable to perform this averaging phase, in alternative embodiments this phase could be skipped and subsequent processing could be performed on data from a single cardiac cycle.

The second phase is edge detection and envelope calculation. In this phase, we delineate, in regards to both amplitude and time, the power and velocity signal tracings vs. time, and thereby separate the sections that represent the blood vessel movement (i.e., the signal) from the noise. One or more noise reducing algorithms may be used during this phase. In one preferred embodiment, two specific edge detection algorithms, referred to herein as algorithm A and algorithm B, are applied to the data. Both algorithm A and algorithm B are applied on the averaged signal and calculate the edge (i.e., envelope) between the signal and the noise in the averaged image.

Algorithm A is a local, one-dimensional method in which the edge ($e_A$) between signal and noise at a given time is defined according to the statistics of the data at the proximity of this time only. This algorithm includes two steps: In the first step, we define, at any given time (ti), a threshold 'thr(ti)' for each power spectrum A(ti) by searching for a region of lowest energy in the proximity of ti. We then set thr(ti) to be equal to the highest power level in this region. Next, we apply thr(ti) on A(ti) and deem all parts of A(ti) above thr(ti) as corresponding to movement regions and all other parts as corresponding to noise.

In the second step of Algorithm A, we refine the initial distinction between flow and noise by using the statistics of noise: In this step, we assume down estimation (flow being included in noise region); adjust envelopes detection to exclude flow pixels from noise regions; and identify pixels of flow in noise regions by their relatively high values. Symbolically, this can be represented by the following three steps:
(a) For each t={1, 2, ... N}, calculate P(t)={mean of A(t) in noise region}
(b) Define a threshold 'thr2' which is based on the average and std of {P(1), P(2), ... P(N)}
(c) For each t' where P(t')>thr2, reduce P(t') by raising upper envelope or lowering the lower envelope until P(t')<=thr2.
For better results, steps (a)-(c) are preferably repeated a number of time (e.g., 10 times).

Algorithm B is an edge detection algorithm that treats the data as two-dimensional image. In this method, the signal is seen as an object surrounded by noise which is segmented out of it, and the edge ($e_B$) is calculated accordingly. This segmentation method is an implementation of the Chan-Vese algorithm. (See Chan T. F., Vese L. A., Active contours without edges. Image Processing IEEE, Transactions on, Volume 10, Issue 2: 266-277 (February 2001), which is incorporated herein by reference).

The edge calculated by Algorithm A ($e_A$=[$e_A$(t1), $e_A$(t2), ... ]) is then combined with the edge calculated by Algorithm B ($e_B$=[$e_B$(t1), $e_B$(t2), ... ]). One suitable approach to combining those two edges is by assuming that the desired edge passes between the two edges that were found. This may be done using a variety of approaches. One approach is take a simple average of the results from algorithm A and algorithm B at each point. Another approach for combining those two edges is to create an array of weights (w=[w(t1), w(t2), ... ]) as follows: (1) the power levels of the image at the gap are integrated along time; (2) the result is linearly transformed to have a maximal value of '1' and minimal value of '0'; and (3) the output for the edge at a time point ti is then defined by the following equation: $e(ti)=w(ti)*e_A(ti)+(1-w(ti))*e_B(ti)$.

Figure 2:
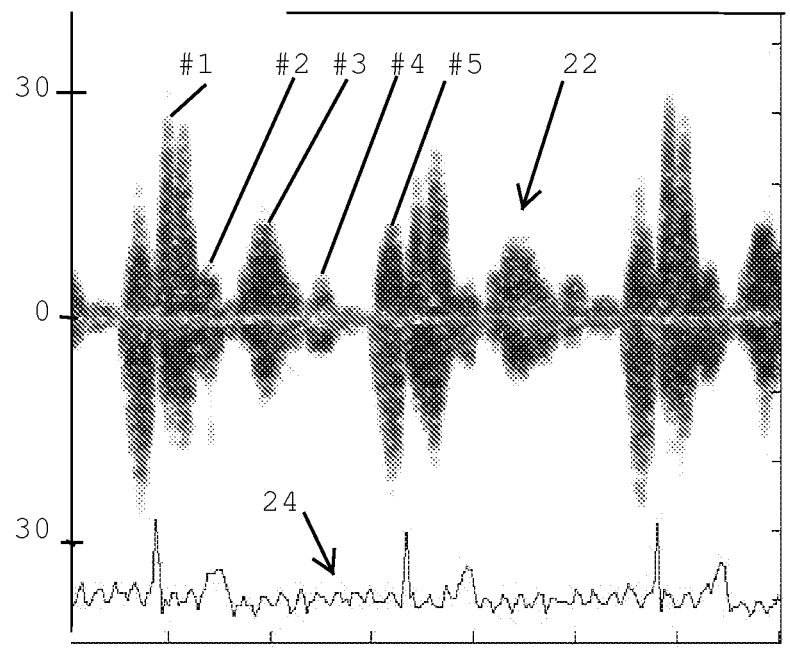
FIG. 2 depicts an example of an output generated by the system of FIG. 1.

The resulting output is preferably smoothened via a one-dimensional median filter (e.g., of order 3) and displayed, and FIG. 2 depicts an example of the resulting output. Note that in alternative embodiments, only one algorithm (i.e., either algorithm A or algorithm B or a different NR algorithm) may be used, either taken alone or combined with other NR algorithms.

FIG. 2 depicts the velocities 22 of the ultrasound reflectors in the right lung of a normal subject obtained using a 2 MHz Doppler ultrasound system with the probe positioned about 3 cm to the right of the sternum and 7 cm up from the level of the tip of the xiphoid bone (about the 4th intercostal space). The ultrasound beam was roughly normal to the chest surface. In FIG. 2, darker regions correspond to higher powers. A conventional ECG 24 is preferably also displayed on the bottom of FIG. 2. Similar recordings were obtained from recordings at depths (gates) of up to 14 cm and from the left lung in areas not dominated by the heart. Maximal signal strength over the right lung was recorded at a depth of 8-9 cm below the surface.

The same pulse repetition frequency (PRF) that is used in conventional TCD systems (i.e., 3-10 kHz) may be used for TPD systems. However, TPD sonograms 22 includes of a number of medium velocity signals that have the same periodicity as the cardiac cycle and usually reach values only up to about 30 cm/sec. Due to these relatively low peak velocities (as compared to Doppler flow measurements in large arteries), the TPD PRF used may be set to a value that is lower than standard pulsed Doppler systems. By lowering the PRF to 1-2 kHz, the effective beam penetration depth is at least doubled as compared with the conventional PRF. This is important as ultrasound velocity in the lung is about 30-50% lower than in fat, muscle etc. thus lowering the effective penetration depth. Preferably, the software is configured to take this lower velocity into account. The transition point where the signals originating in the lung can be detected by recognizing the shallowest point at which the lung signals (i.e., signals with very large returns) appear. Note that measurements from different lung depth result in very similar tracings, and that the traces for other apparently normal subjects had generally similar characteristics.

Figure 3:
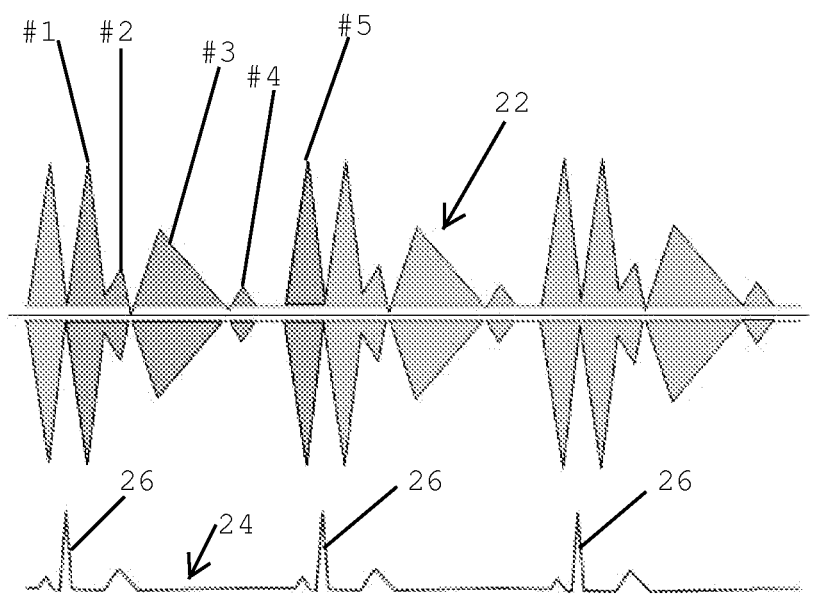
FIG. 3 is a schematically illustration of five features in the output shown in FIG. 2.

It is seen that, at each polarity (positive or negative), one can usually identify five significant features with relatively high energy and a roughly triangular shape. These five features are schematically illustrated and numbered #1-5 in FIG. 3. Each of these features includes a positive component (i.e., positive velocities, indicating that the flow direction is towards the probe) and a corresponding negative component (i.e., negative velocities, indicating that the flow direction is away from the probe), with a high degree of positive/negative symmetry. Thus, each of these features indicates simultaneous movements in opposite directions. As seen in FIG. 3, these features are synchronous with the cardiac cycle (note the R waves 26 in the ECG 24).

Theory of Operation

The above described signals recorded over the lungs appear to have a unique origin. As is well known the lungs consist of a very large number of alveolar ducts, alveolar sacs and alveoli which can be regarded as miniature gas volumes encapsulated by a very thin membrane. The alveoli, which can be assumed to be reasonably represented by spheroids, have dimensions in the range of 50-150μ. When exposed to ultrasound waves these natural lung components resemble in many respects ultrasound contrast media used in sonography. (Ultrasound contrast agents are gas-filled microbubbles with a high degree of echogenicity, i.e., the ability of an object to reflect the ultrasound waves.) The echogenicity difference between the alveoli and soft tissues is very large and therefore most of the energy is reflected.

Although scattering makes it impossible to obtain ultrasound images of lung structures, it is actually helpful in detecting movement of the highly reflective border between blood vessels and/or soft tissue (collectively referred to herein as blood vessels/soft tissue) and alveoli. Movements of this border are induced by respiration and even more so by cardiac contraction and mechanical pulse waves travelling in the blood and the pulmonary blood vessels. It is well known that the pulmonary blood vessels have a very high compliance (i.e., much larger than that of the systemic circulation), and the air filled alveolar tissue surrounding the vessels is highly compressible. Thus, pressure waves in the pulmonary arteries and veins result in significant changes in their diameter. These changes in turn move the highly reflective border, compressing and moving the alveoli, alveolar sacs, etc. in their vicinity. As the ultrasound propagation velocity in tissue and air are very different, there is a mechanical coupling mismatch at their border resulting in high echogenicity and strong ultrasound reflections, which in this case is from a moving reflector that results in Doppler shifts. These reflections are often on the order of 100 dB above the noise level (in comparison to typical intensities measured from blood flowing in arteries, which are in the range of 20-40 dB above noise level). Because these signals are so strong, the returns are picked up by the Doppler system even though they may be partially masked by a layer of stationary lung tissue, which attenuates ultrasound energy by about 40 dB/cm.

Figure 4A:
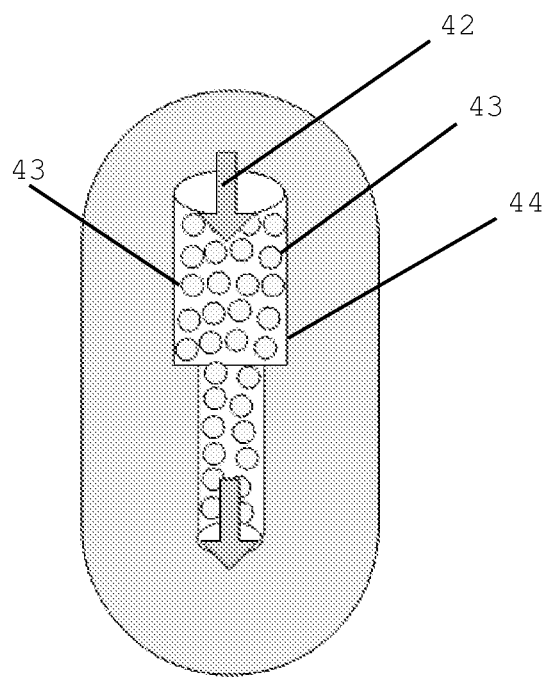
FIG. 4A depicts the "classical Model" of clinical Doppler measurements.
Figure 4B:
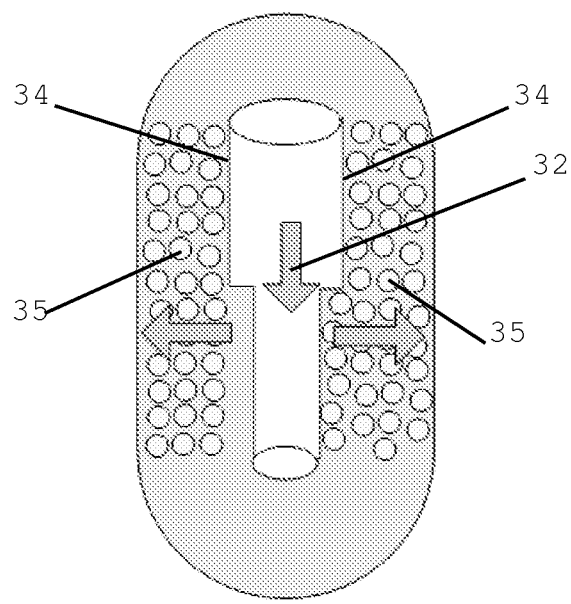
FIG. 4B depicts the origin of the Doppler signals picked up using TPD.

FIG. 4A and FIG. 4B illustrate the differences between conventional Doppler signals and the signals picked up by TPD through the chest wall. FIG. 4A illustrates the "classical Model" of clinical Doppler measurements in which the device measures the Doppler frequency shift resulting from blood flow 42 in arteries and veins, or more specifically from the movement of the erythrocytes 43 (which reflect the ultrasound waves) through those vessels 44.

FIG. 4B illustrates the origin of the Doppler signals picked up using TPD. Here the changes in pressure induce changes in vessel diameter because as the heartbeat generates pressure pulses that urges the blood 32 through the vessel, the vessel walls 34 momentarily bulge outwards and compress the air filled alveoli, alveolar sacs, etc. 35 that surround them. The Doppler shifts of the reflected ultrasound induced by the moving border between the blood vessels/soft tissue and the alveoli are translated to power-and-velocity vs. time plots and displayed by the TPD system. It is expected that the majority of these signals are generated by small and intermediate size arteries and veins. A unique feature of signals generated in this mode (as opposed to those generated by the flow of blood in the rest of the body) is their bi-directionality. This phenomenon is likely because the lung parenchyma encircles the blood vessels/soft tissue from all sides so that regardless of the relative beam direction, the closer borders move towards the beam source while those at the far side move away from it. As a result, similar signals of opposite polarity are generated. In some cases, as depicted in FIG. 2 the signals seem almost perfectly symmetrical. Such symmetry is rarely seen in non-pulmonary Doppler records.

It is notable that with conventional Doppler measurements of blood flow through vessels, where the movement is the blood flow itself, the probes are positioned so the ultrasound beam is as parallel as possible to the flow axis to obtain maximal velocity. In contrast, the motion that gives rise to the TPD measurements described herein is perpendicular to the direction of blood flow, so the optimal position is normal to the flow axis and parallel to the vessel radius. But since there are so many blood vessels in the lungs, positioning is less critical in the context of TPD (as compared to conventional Doppler measurements of blood flow through vessels).

Since the features in FIG. 2 always have a repetition cycle corresponding to the R-R interval of the ECG 24, we have concluded that they must originate from structures that reflect ultrasound energy while moving in synchrony with the heart beat. These entities could be the heart itself, the blood flowing in the pulmonary blood vessels, the pulsating blood vessels, or their junctions with alveoli, alveolar sacs, air, etc.

Figure 5B:
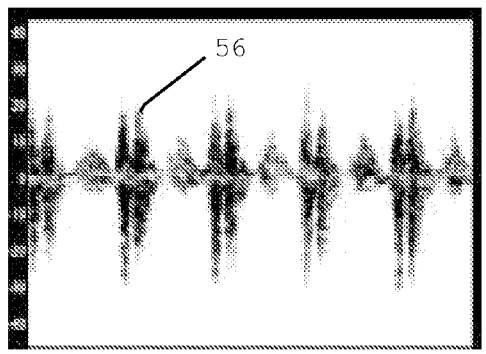
FIGS. 5B-E are TPD outputs for normal breathing and during various respiratory maneuvers.
Figure 5C:
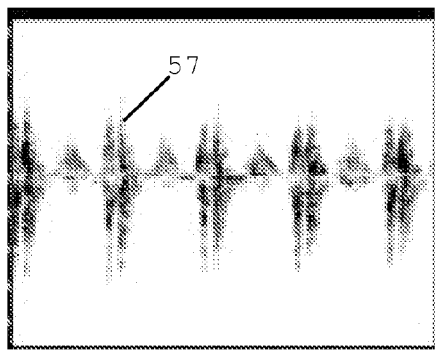
Figure 5D:
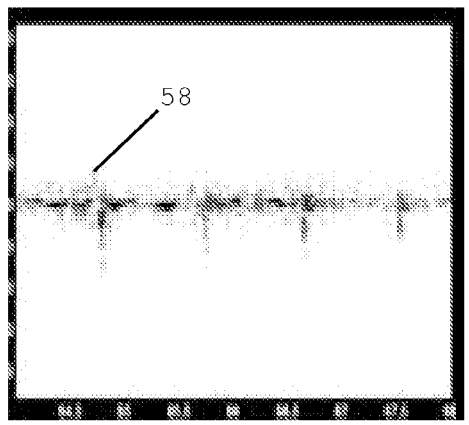
Figure 5E:
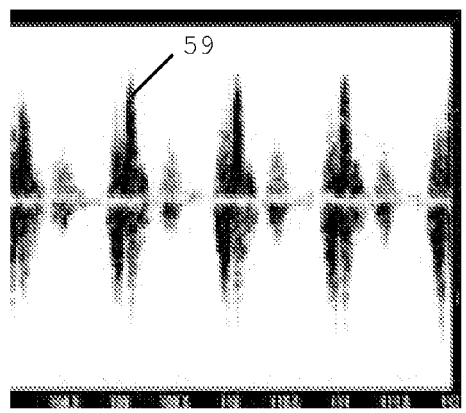

The recorded signals will be referred to as—Lung Doppler Velocity Signals, (LDVS). FIG. 5A compares a typical LDVS 52 of a normal subject with tracings 55, 56 of blood flow velocity in both a pulmonary artery and vein, for a single cardiac cycle, with the cardiac cycle durations normalized to the same time scale (note the R-waves 26 of the ECG 24). Significant correlation is present. FIGS. 5B-E compare the LDVS 56 of normal breathing (FIG. 5B) with those recorded during various respiratory maneuvers over a number of cardiac cycles. For example, during breath-holding at FRC (functional residual capacity) (FIG. 5C), the features 57 have normal shape and velocity but attenuated intensity. During a Valsalva maneuver (FIG. 5D) in which the chest cavity pressure is greatly elevated, the features 58 are seen to virtually disappear. In contrast, during a Muller maneuver (FIG. 5E), which generates negative pressure within the chest cavity, both the velocity and signal power of the LDVS 59 increase.

The synchronization of the five features (#1-5) with the heart beat and associated mechanical events indicates that the signal source is related to pulsations generated by the heart and blood vessels, and the strong modulation of the features by respiratory maneuvers (see FIGS. 5C-E) indicates that the state of the lung parenchyma strongly affects their shape. The fact that similar signals are recorded throughout the lungs, in spite of the strong mechanical dumping properties of the lung parenchyma, rules out direct involvement of the heart and large blood vessels. Thus, it is most likely that the spread of the pulsations is by propagation along the blood vessels in the lungs, including the relatively small ones.

Based on the theory of operation set forth above, we interpret the five features depicted in FIGS. 2 and 3 as follows: Feature #1, which is usually very prominent, appears shortly after the R wave, and coincides with the systolic ventricular contraction. Feature #2, which has lower peak velocity, coincides with the T wave of the ECG and repolarization and ventricular relaxation. Feature #3, which is often double humped and is of relatively longer duration, seems to appear mainly during the diastolic rapid filling phase. Feature #4, which typically has a low peak velocity, corresponds to the diastasis, the latter part of which is often not associated with a detectable signal. Feature #5, which is usually of high peak velocity, coincides with atrial contraction.

The relative amplitudes, rise times and fall times, durations etc. of these five features thus provide information regarding the blood flow hemodynamics, passive mechanical properties of the various cardio-vascular system components, as well as the active (contraction) forces. In addition, the displays provide information related primarily to the pulmonary system.

To verify the theory that the returns are generated by a moving tissue-air boundary, a Doppler sonogram was made using a phantom where pseudo-blood (Doppler test fluid 707, ATS Laboratories Inc. CT, USA) incorporating miniature air bubbles (under 0.5 mm) was flowing in an appropriate vessel. In the sonogram the bubbles appear as bright "blips." The power spectra of the flowing pseudo blood and bubbles reveal that the peak power generated by the moving air bubbles is about 40 dB higher than that of flowing pseudo-blood and coronary flow recorded under similar conditions. These results are compatible with the theory set forth above.

Measurements were taken on 10 normal volunteers aged 27-72 over the right or left lung by means of an ultrasound sensor positioned over the chest wall of a sitting or supine subject. A 21 mm, 2 MHz sensor having a focal length of 4 cm was impedance matched with the chest wall by standard ultrasound gel. Measurements were made from different positions over the chest wall using a pulsed TCD device (Sonara/tek, Viasys, Madison, Wis., USA) at a pulse repetition rate (PRF) of 3 kHz. The transmitted pulse power was up to 10% of the allowed maximal ISPTA.3 (492 mW/cm$^2$). The subjects were connected to a standard three lead ECG (Norav Medical Ltd, Yokneam, Israel) the output of which was included in the display.

Further verification of the theory proposed above follows from the observation that bidirectional wall movement signals have been reported from pulsating peripheral arteries. Note that as the compliance of the pulmonary vessels is much higher than that of the systemic vessels, the changes in vessel diameter are significant despite the relatively low pulmonary pulse pressure. Thus, in spite of the significant attenuation caused by the lung parenchyma, the LDVS have relatively high power (80-90 dB) when they reach the body surface. The LDVS peak velocity values may reach of 20-40 cm/sec, values that are consistent with the arterial wall motion velocity as reported in the literature. The pulse wave propagation velocity that is determined by the vessel compliance can be computed on the basis of the delays between the recorded R wave and timing of feature #1. Note that the Doppler signals reflect blood vessel expansion with the pressure pulse wave that travels very rapidly along the highly compliant lung vessels. As the speed of pulse propagation in the blood vessels is 2-5 m/s, typical delays are on the order of 10-40 msec.

Observing the resulting velocity-and-power vs. time traces can provide diagnostic information on the mechanical properties of the pulmonary parenchyma, in general and at specific locations when those traces deviate from the expected normal traces. This may include information related to the tissue structure (which may be relevant to emphysema, fibrosis, atelectasis, etc.), vasculature, or the presence of fluid in or around the alveoli (as in congestive heart failure or pneumonia, vascular events such as emboli & hemorrhage), etc. These deviations from normal can result from changes in the elastic properties as well as the mass of the various tissue elements as well as their spatial distribution. Such changes will result in global or local corresponding changes in the power spectra profiles, time constants, durations, or amplitudes (relative or absolute) of the traces. Physiological manipulations such as deep inspiration, forced expiration, breathe holding, Valsalva maneuvers, exercise, etc. may be used to enhance the diagnostic capabilities. Note that the ultrasound waves reflected from any intra-pulmonary element are modified as they pass through the lung parenchyma that intervenes between them and the chest wall. This tissue acts as a mechanical filter of specific characteristics. These characteristics depend on the state of the relevant parenchyma, such that the power spectra of the signals that pass through this filter reflect on the filter characteristics for acoustic signals as described by Gavriely N., Y. Palti & G. Elroy (Spectral Characteristics of Normal Breath Sounds, J. Appl. Physiol. 50: 307-314 (1981), which is incorporated herein by reference).

Figure 6:
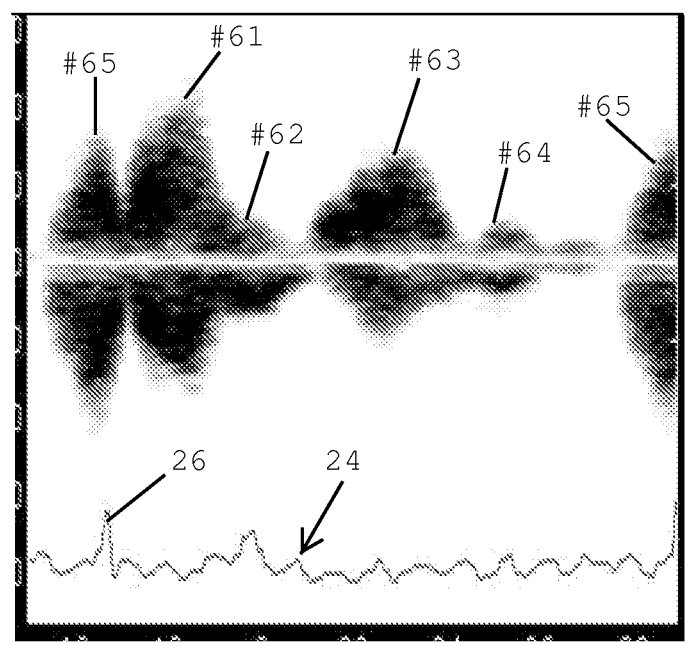
FIG. 6 depicts a TPD output averaged over ten cardiac cycles from a normal subject.

Optionally, the signals from a single subject may be averaged over a number of cardiac cycles using the R wave 26 of the ECG 24 as a reference point. FIG. 6, for example, depicts an average 62 of ten cardiac cycles from a normal subject, recorded over the right lung. Five features #61-65 can be seen, corresponding to features #1-5 discussed above. The traces were generally similar for other normal subjects.

Detection and Characterization of Cardiac and Pulmonary Function

One useful application of the TPD system described herein is as a tool for indirectly ascertaining the function of the cardiac and pulmonary systems through TPD measurements of the lungs. This is possible because the outcome of the cardiac activities propagate along the pulmonary blood vessels from their origin in the heart to the whole lung volume. A number of clinically significant deviations from normal mechanical cardiac activity can be detected and characterized using TPD in this way, and some examples are given below.

Based on these examples, a Transthoracic Cardio-Pulmonary Monitor ("TCPM") can be implemented to provide information regarding the cardio-pulmonary state of patients. The hardware block diagram for a TCPM is the same as the TPD System depicted in FIG. 1, but additional functionality is built in to the computer 13. For example, the computer 13 may be configured to report the status of the patient's vital signs (e.g., heart rate, respiration rate, etc.) as explained below. The TCPM may also be used to determine the origin of cardiac contractions, the magnitude of cardiac contraction force, the respiration rate and depth, and the state of the pulmonary parenchyma (including fluid accumulation and consolidation). Optionally, the computer 13 may be programmed to identify situations that may accompany a problematic health condition, and to sound alarms and/or capture data when such situations are detected. The TCPM can be used as a stand-alone diagnostic tool or in combination with other monitors.

Note that the shapes of the five features (#1-#5) contain information regarding cardiac activity and the compliance of the pulmonary blood vessels. The latter can indicate the presence of changes in the pulmonary vessels in patients with pulmonary hypertension and diseases of connective tissue, etc.

Figure 7A:
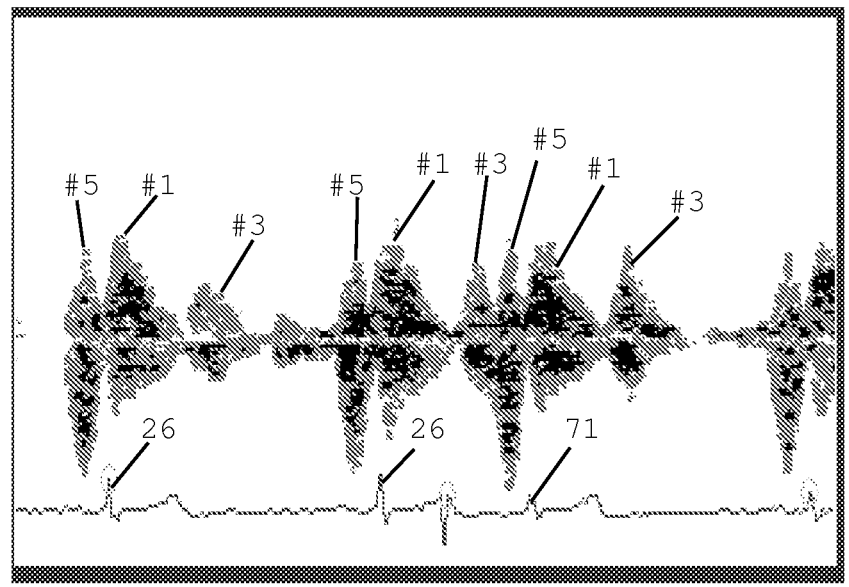
FIG. 7A depicts a TPD output for a normal sinus rhythm followed by a propagating atrial extra-systole.
Figure 7B:
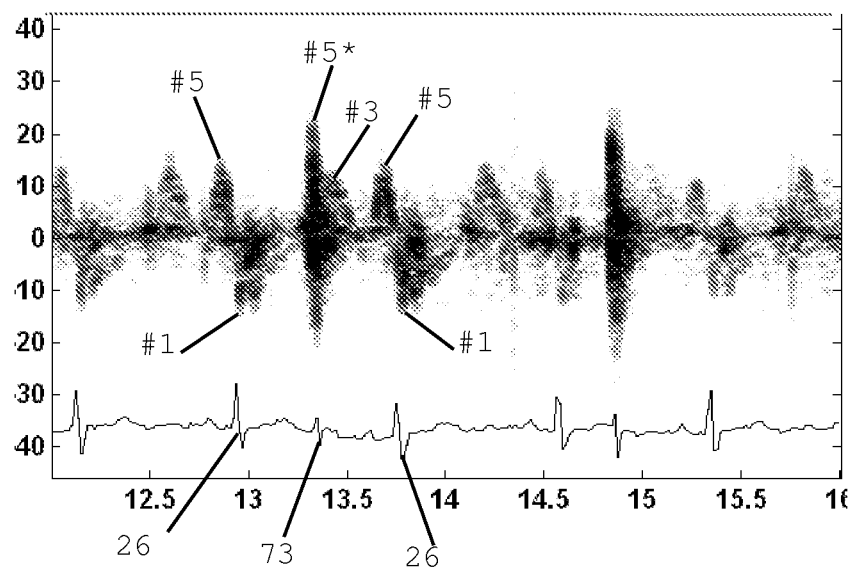
FIG. 7B depicts a TPD output when an atrial non-propagating extra-systole is present.

One abnormality that can be detected using a TCPM is the presence of extra systoles. FIG. 7A depicts the changes from the normal pattern of lung signals in cases of arrhythmia due to atrial extra-systoles, which is a type of additional abnormal cardiac contraction. The left side of FIG. 7A depicts signals typical of a normal sinus rhythm, and the right side depicts the appearance of an atrial extra-systole 71 (i.e., the signals generated by an early electrical beat produced by the sinus node) that propagates to the ventricles. These signals are basically a duplicate of the normal rhythm complex, i.e. they include an extra atrial contraction (feature #5) followed by an extra ventricle contraction (feature #1) and ventricle relaxation (feature #3). When they occur early enough, the atrial contraction signal (feature #5) may superpose in time over previous ventricular relaxation (feature #3). FIG. 7B illustrates the characteristics of a signal produced by an atrial extra-systole 73 resulting in an atrial contraction (feature #5) that does not propagate from the atrium to the ventricles, as manifested by the absence of features #1 and #3 after the abnormal additional feature #5*.

Figure 8:
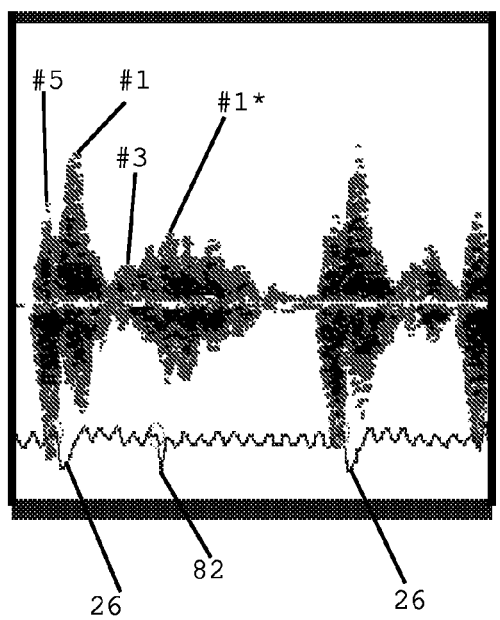
FIG. 8 depicts a TPD output when extra-systolic contractions are present.
Figure 9:
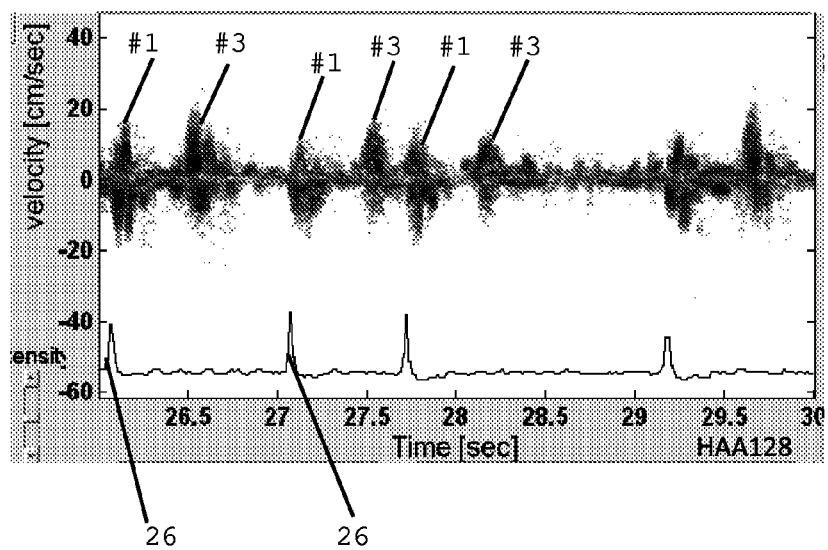
FIG. 9 depicts a TPD output when atrial fibrillation occurs.

FIG. 8 illustrates signals produced by Extra-Systolic contractions (feature #1*) generated by electric abnormal activity 82 in the ventricle. FIG. 9 depicts signals corresponding to contractions of ventricular origin (#1) in a patient suffering from atrial fibrillation. This condition is apparent from FIG. 9 because feature #5 (representing atrial contraction) is missing. It is also seen that the characteristics of the ventricular extra-systoles are very different from those of the atrial extra-systoles, reflecting the large differences of the nature of the mechanical activity. It is also seen that the characteristics of the ventricular contraction and relaxation (features #1 and #3) are quite similar to those of normal ones. Such recorded tracings can help the physician determine the pathway of propagation of the abnormal activity.

The presence of any of the abnormal features discussed above in connection with FIGS. 7A, 7B, 8, and 9, can therefore be used as an indication that the patient has the corresponding problem. This may be accomplished visually, by looking at the displays and recognizing the relevant features. In alternative embodiments, pattern recognition software may be used to recognize the relevant features automatically.

One way to detect abnormal heartbeat features of a patient is to use the ultrasound probe described above to obtain Doppler ultrasound power and velocity data for a period of time that corresponds to a plurality of cardiac cycles. The obtained power and velocity data are processed using at least one noise reduction algorithm, including but not limited to the ones discussed above. Features in the power and velocity data that occur once per cardiac cycle (e.g., features #1-5) are identified. Timing between the identified features is then determined. Based on this timing, the expected arrival time of a given feature can be predicted. For example, if feature 1 is being tracked, and the spacing in time between successive occurrences of feature #1 is 1 second, the system can predict that a new feature #1 will arrive 1 second after the previous feature #1. If, instead, the new feature #1 arrives after only ⅓ sec, the system recognizes the early arrival as an anomaly and generates an appropriate outputting indicating that the particular feature was detected at an unpredicted time. Examples of suitable outputs include alarms, printouts, or flags that initiate a data storage routine (so that the anomaly can be viewed by an operator at a later time).

Since the alveoli and boundary movement are detected, a TCPM may also be used to monitor the heart rate. As the signals recorded over the lung are in complete synchrony with the heart beat, the heart rate can be determined independently from the ECG (which often produces incorrect results due to motion artifacts).

One way to determine the heartbeat rate of a patient is to use the ultrasound probe described above to obtain Doppler ultrasound power and velocity data for a period of time that corresponds to a plurality of cardiac cycles. The obtained power and velocity data are processed using at least one noise reduction algorithm, including but not limited to the ones discussed above. Features in the power and velocity data that occur once per cardiac cycle (e.g., features #1-5) are identified. Timing between the identified features is then determined. For example, if feature 1 is used, and the spacing in time between successive occurrences of feature #1 is 2 seconds, then the heart rate would be 30 beats per minute (bpm). An indication that the heart rate is 30 bpm is then output.

Figure 10:
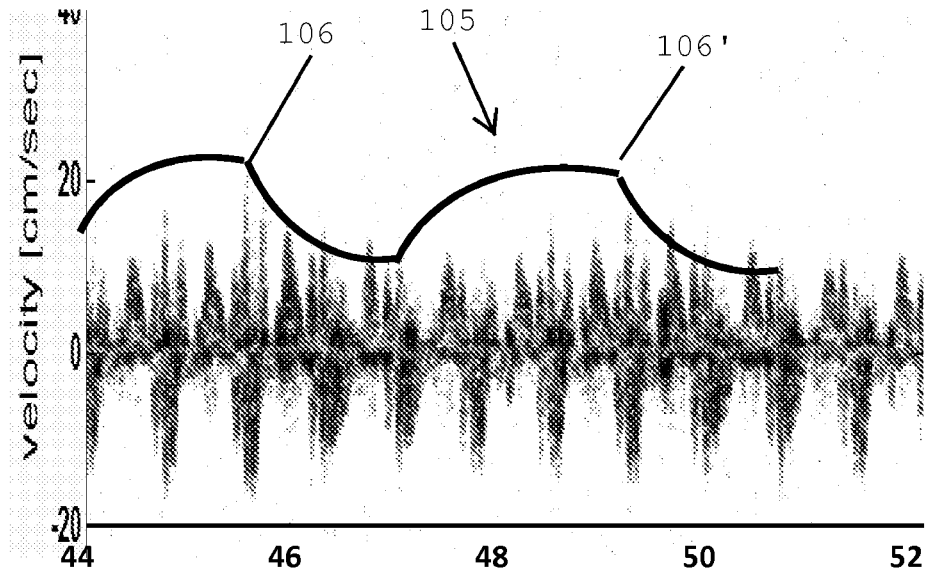
FIG. 10 depicts using TPD to determine the patient's respiration rate.

The TCPM may also be used to determine a patient's respiration rate. FIG. 10 illustrates using the TCPM to determine the patient's respiration rate by following the changes in both the velocity and power of the signals recorded, e.g., over the right chest. These changes are due to the changes in the lung air/tissue volume ratio during the respiratory cycle as well as the modulation of the blood pressure and cardiac output with respiration.

One way to determine the breathing rate of a patient is to use the ultrasound probe described above to obtain Doppler ultrasound power and velocity data for a period of time that corresponds to a plurality of cardiac cycles. The obtained power and velocity data are processed using at least one noise reduction algorithm, including but not limited to the ones discussed above. The envelope 105 of the power and velocity data with respect to time is then extracted from the LDVS using an appropriate envelope detection algorithm. The parameters of the envelope detection algorithm should be set to pass frequencies that are slow enough to relate to breathing and block frequencies that are fast enough to relate to heat-beats. For example, since breathing will usually be slower than 15 breaths per minute, frequencies of less than 0.25 Hz should be passed by the algorithm. And since breathing will rarely be faster than 90 breaths per minute, frequencies of more than 1.5 Hz should be blocked by the algorithm. The cutoff between the pass band and the stop band should preferably be selected somewhere between those two frequencies. A periodic feature of the extracted envelope, such as the highest peak 106, 106' or the lowest trough, is identified over multiple breathing cycles and timing between two or more occurrences the identified feature is determined. An indication of the breathing rate is then output based on the determined timing. For example, if successive peaks 106, 106' are 10 seconds apart, it would mean that the breathing rate is 6 breaths per minute.

Figure 11:
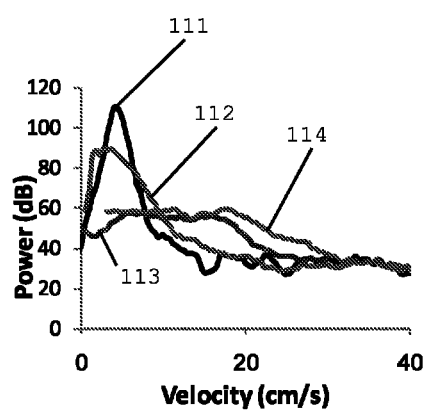
FIG. 11 depicts the measured Doppler power spectra for pseudo blood.

The TCPM may also be used to detect a fibrotic lung. The Doppler power spectra FIG. 11 of the flowing pseudo blood with bubbles reveal that the peak power 111 generated by the flowing bubbles is similar to that of the LDVS signals 112 recorded over the lung, both reaching values of 80-110 dB. Very strong reflections produced by air-tissue interfaces, for example, pleural surface—chest wall, are well known. These reflections also serve as the basis for ultrasound contrast materials that consist of small, membrane encapsulated, air bubbles that can be regarded as analogue to the lung alveoli. These power values are much higher than those of blood flow, for example, the power spectrum 113 of coronary blood flow obtained under similar conditions.

However, in the special case of the relatively transparent fibrotic lung, blood flow 114 in the large pulmonary blood vessels can be seen through the lung. Note also that the shape and frequency content of the power spectrum of the LDVS is quite different from those typical of blood flow, the latter having a plateau reflecting the parabolic nature of the blood flow profile. These deviations from the expected values can be detected by selecting a threshold that is appropriate for the patient (e.g., based on age, condition, etc.) and generating an alert when the threshold is exceeded.

Figure 12:
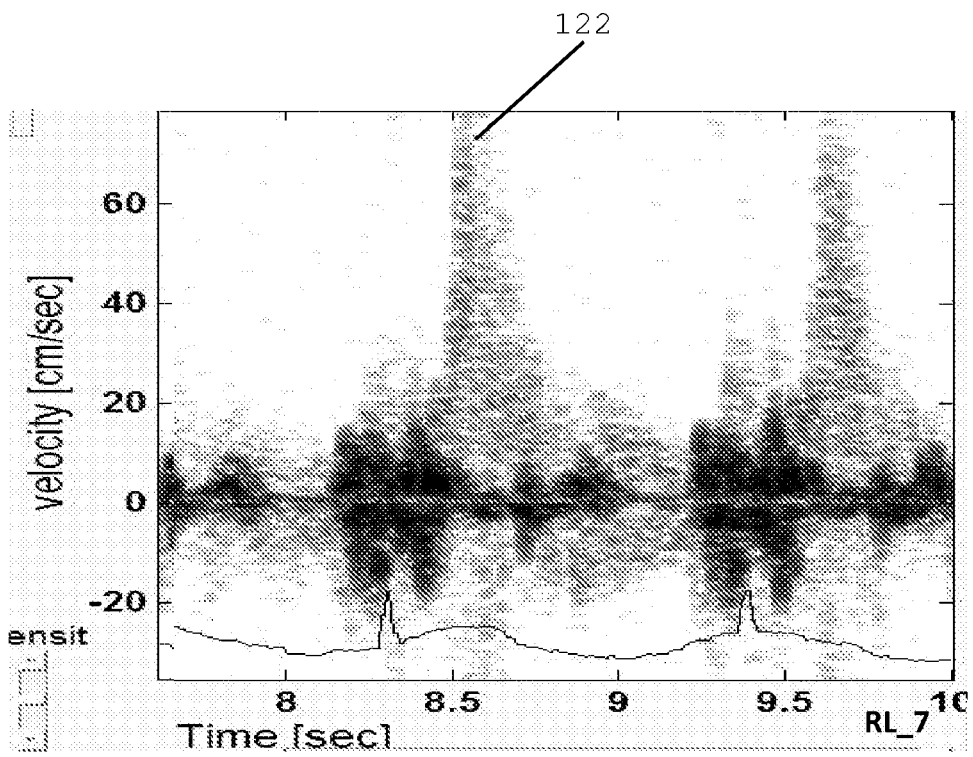
FIG. 12 depicts a TPD output recorded from a patient with pulmonary fibrosis.

FIG. 12 depicts LDVS recorded from a patient with pulmonary fibrosis. In such patients the connective tissue strands within the lung parenchyma, act as "wave guides" through which the ultrasound energy travels deep into the lung and back without being attenuated by the alveolar air. Thus, in this case the lung is semi-transparent such that the tracings include signals generated by blood flow in the deeply located main pulmonary blood vessels. Note that the blood flow velocity 122 is much higher than in a healthy lung, while the Doppler power is significantly lower.

From the above it can be seen that the LDVS contain important structural and functional information that may be of high diagnostic value for both the pulmonary and cardiac systems. The signal power reflects the level of signal attenuation which depends on the structural nature of the lung parenchyma. It is well established that the attenuation increases when the air/tissue ratio increases, which can be indicative of, for example, pneumothorax or severe asthma attack. Conversely, the attenuation decreases in lung consolidation or when fluid accumulates as is expected to be the case of pulmonary edema and CHF, for example. Variations in the expected attenuation of the LDVS can therefore be compared to suitable thresholds by the TCPM, and appropriate outputs and/or alerts can be generated in response. TCPM may also be used to monitor the amplitude of the cardiac muscle contraction, because the power of the reflected Doppler signals is proportional to the magnitude of the contraction.

Figures 13A, 13B:
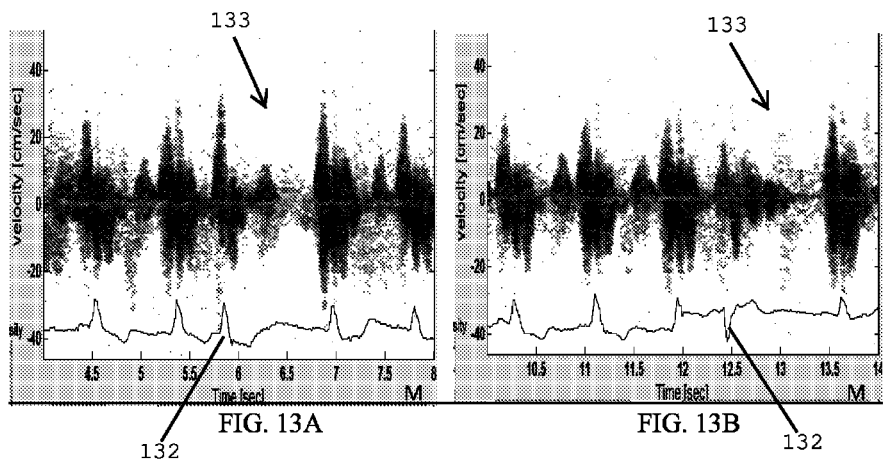
FIGS. 13A and 13B depict lung Doppler signals recorded from two patients that have extra-systoles.
Figures 13C, 13D:
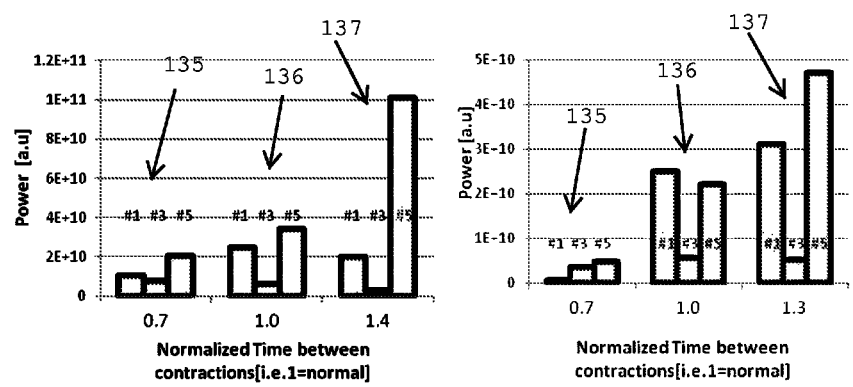

FIGS. 13A and 13B depict lung Doppler signals recorded from the right lung of two patients that have extra-systoles 132. We see that when an extra-systole 132 occurs relatively early in the cardiac cycle, i.e. when a significant fraction of the cardiac muscle is in the relative refractory period and therefore the contraction force is diminished, the recorded signals 133 have a corresponding lower velocity and power. FIGS. 13C and 13D depict bars representing the reflected Doppler power of features #1, #3, and #5, with the abscissa representing time relative to the normal R-R interval. The bars 136 for signals recorded from a beat that follows a normal contraction, having an inter-contraction interval of 1, are generally larger than the bars 135 recorded from an early contraction (inter-contraction interval of 0.7). In contrast, beats that occur after an interval longer than the normal inter-contraction interval, (1.3-1.4) i.e. following a compensatory pause, are generally larger, as indicated by the bars 137. This result is consistent with the more forceful contractions that are known to occur under such conditions. Abnormal conditions can therefore be detected, and can be used to trigger notifications and/or alarms as appropriate. All in all we see that the LDVS power depends on the magnitude of the cardiac muscle contraction. The TCPM can therefore be used to determine the magnitude of the cardiac muscle contraction.

Figure 14:
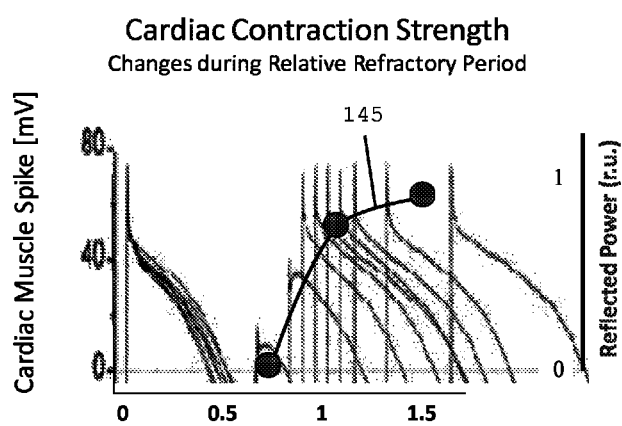
FIG. 14 depicts how power correlates to cardiac contractile force

TCPM may also be used to measure the cardiac contractile force. Cardiac contractile force is well expressed in the power of the reflected ultrasound wave as expressed in the color or intensity of the tracing and in the quantitative power parameter outputted by the TCPM. FIG. 14 depicts the reflected ultrasound Doppler Power of feature #1 (curve 145), which is produced by the cardiac systole, as a function of its time of appearance during the cardiac muscle relative refractory period. The data points on curve 145 represent the power of feature #1 for the extra systoles. It can be seen that the power, as determined by the TCPM, correlates well with the changes in the amplitude of the cardiac muscle electric activity during the relative refractory period. The cardiac contractile force is proportional to the amplitude of this activity (see Cardiovascular Physiology, Berne & Levy) so the overall results demonstrate that the TCPM can detect changes in cardiac contractility. Here again, abnormal conditions can be detected, and can be used to trigger notifications and/or alarms as appropriate.

Figure 15:
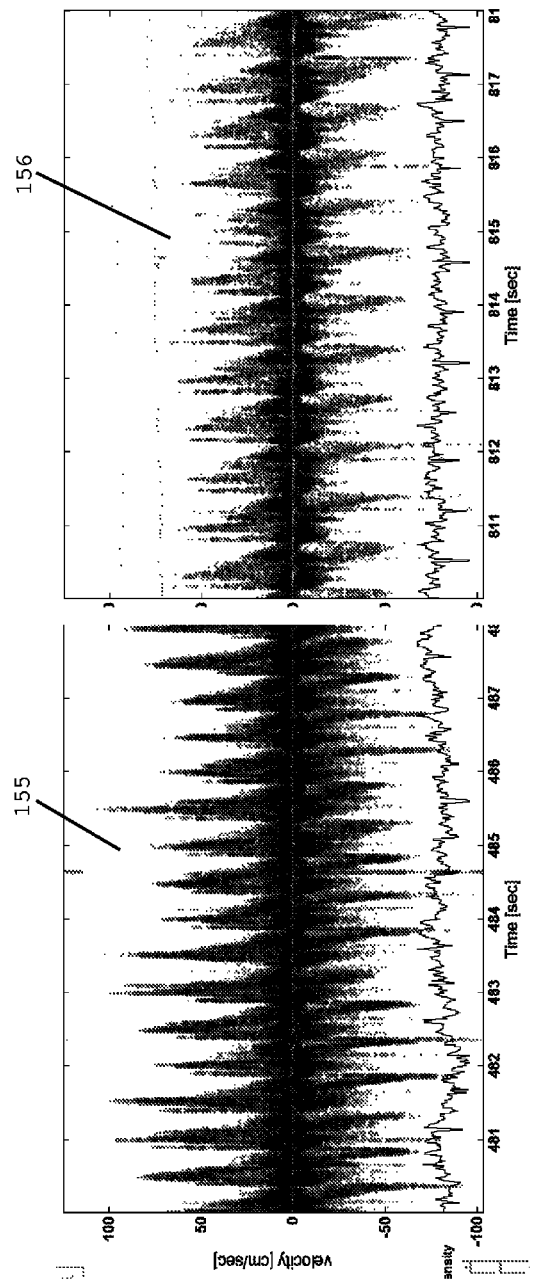
FIGS. 15A and 15B depict a TPD output obtained from a patient with an unstable cardiac condition.

TCPM may also be used to measure the flow velocity in the LAD coronary artery. FIGS. 15A and 15B depict two typical displays obtained from one patient with an unstable cardiac condition, recorded about 30 minutes apart. In FIG. 15A, the display 155 shows an average peak velocity of 75 cm/sec and an average total power of 70 dB. In FIG. 15B, the display 156 shows an average peak velocity of 54 cm/sec and an average total power of 68 dB. We therefore see the tracings of the flow velocity in the coronary artery (LAD) together with the TCPM determined change in Velocity and Power parameter values. Such coronary flow tracings can serve to follow changes in a patient's blood perfusion/oxygenation and detect dangerous declines due to spasms, occlusions, low aortic pressure, etc. Monitoring of coronary flow preferably uses an additional, coin-shaped, ultrasound Doppler probe positioned on the left chest over the LAD. Once again, abnormal conditions can therefore be detected, and can be used to trigger notifications and/or alarms as appropriate.

Figure 16:
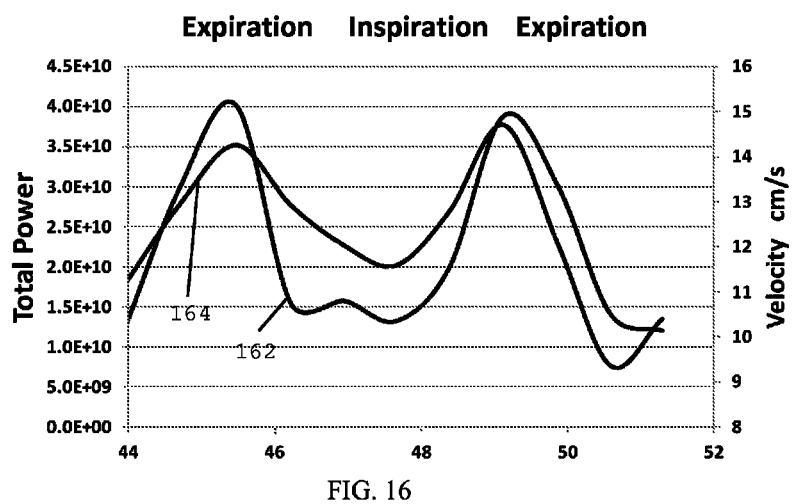
FIG. 16 depicts how power and velocity vary with the depth of respiration over time.

TCPM may also be used to measure a patient's respiration volume or depth, which may be indicative of the state of critically ill patients. In FIG. 16, curve 162 shows the velocity (using the scale on the right) and curve 164 shows the power (using the scale on the left), and these curves vary in synchrony with the breathing cycle. This can be used to deduce information about the breathing cycle, and can be used an additional way to determine the breathing rate (e.g., by determining the period of either the velocity curve 162 or the power curve 164). Yet again, abnormal conditions can be detected, and can be used to trigger notifications and/or alarms as appropriate.

Figure 17:
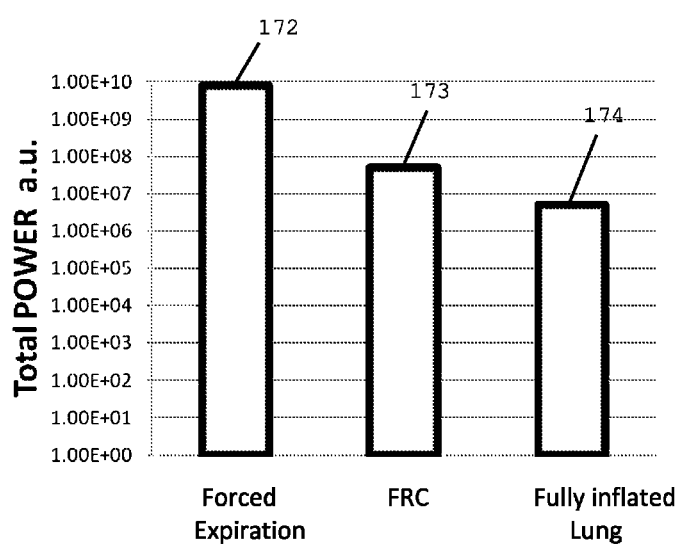
FIG. 17 depicts how power is affected by the relative lung volume.

FIG. 17 illustrates that the total lung signal power, as determined by the TCPM, is strongly affected by the relative lung volume—the larger the volume, the stronger the signal attenuation and the lower the power. Note that the ordinate is a logarithmic scale, i.e. the power changes by two orders of magnitude between a fully inflated lung (bar 174) and the lung volume during forced expiration (bar 172), with the power at FRC (bar 173) lying between those two extremes.

TPD measurements may be taken from different lung depths, and such measurements usually show very similar tracings indicating a wide spread of the signals in the lung volume. Measurements may also be taken from different positions on the subjects' body, such as over the intercostal spaces (e.g. between the 2nd and 3rd ribs or between the 5th and 6th ribs) as well as from positions over the ribs. When such measurements are taken at multiple positions, in some cases there are significant differences between the signal shapes, velocities, and power measurements taken at each position. These distinctions may be detected using TPD and relied on to diagnose certain physiological conditions, either visually from the displayed power-and-velocity vs. time displays, or automatically using appropriate pattern recognition or parameterization software, as described in U.S. application Ser. No. 12/912,988, which is incorporated herein by reference.

Automatic Feature Recognition

Figure 18:
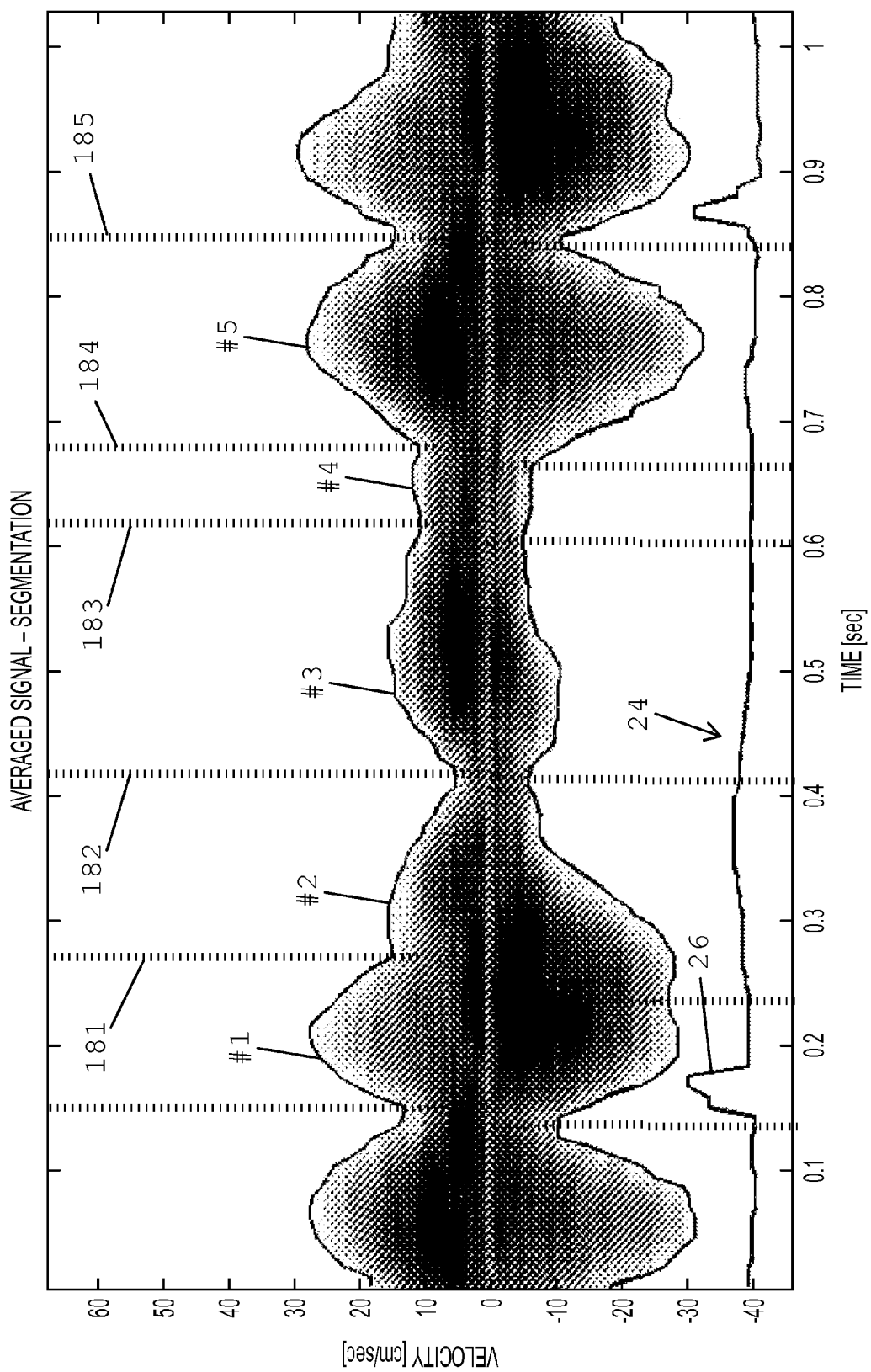
FIG. 18 depicts the boundaries between features determined by an automatic feature recognition algorithm.

The discussion above makes frequent references to features #1-5. Optionally, software that recognized the delineation between each of those features may be implemented in the personal computer 13 (shown in FIG. 1). Automatic feature recognition ("AFR") may be implemented on the averaged signals discussed above in connection with FIG. 6, on a single signal (e.g., as depicted in FIG. 2), or after the averaging operation contained within the NR (i.e., the first phase of the noise reduction routine discussed above). FIG. 18 is an example of automatic feature recognition based on the latter. In FIG. 18, each of the features #1-5 is bounded by two local minimum points on the calculated envelope, and defined according to the relative location of its peak velocity (i.e., maximum point) and the averaged signals' ECG waveforms. These local minima define the transitions 181-185 between the various features and are denoted by dashed lines in FIG. 18. In a regular cardiac rhythm, the features are defined in relation to the ECG signal 24 as follows: #1—the segment with the first velocity peak after the first R-wave 26; #2—the segment with the first velocity peak after feature #1 but preceding the ECG's T-wave; #3—the segment with the first velocity peak after the T-wave ends; #4—the segment bounded between feature #3 and feature #5; and #5—the segment with the velocity peak that immediately precedes the next R wave and next feature #1.

AFR can be useful because the absolute and relative calculated parameters that characterize these segments may be used to classify and diagnose a pathology and its location. These parameters are useful for automated recognition of various conditions that rely on parameterization, discussed below.

Paramaterization

Parameterization may be used to characterize the various features so as to diagnose and estimate the extent of various pathologies such as COPD, Sarcoidosis, Fibrosis asthma, emphysema, pulmonary hypertension, pulmonary embolism, tumors, arteriosclerosis of pulmonary vessels, atelectasis, cardiac contractile dysfunction, and arrhythmia etc. Quantification of the various parameters may be done on specific segments and the relations between them, as well as on the variability of the signals in the original spectrogram (i.e., before it was averaged). The parameterization may be implemented using the approaches described in U.S. application Ser. No. 12/700,828 ("the '828 application"), filed Feb. 5, 2010, which is incorporated herein by reference.

Some of the data is derived from the power spectra themselves as provided by the Doppler measurements. The features of these power spectra may also be parameterized, for example the power at specific velocities, the average slopes of the curves, the number of different slopes at the positive and negative features etc. Parameters may also be derived from the velocity and power versus time tracings. The tables below contain examples of parameters that may be used to parameterize the TPD results, and their definitions:

| Velocity Features: |
|---|
| $\text{peak\_velocity}\{PDS_i\} = \max(\text{envelope}\{PDS_i\})$ |
| $\text{peak\_velocity\_ratio}\{PDS_{i,j}\} = \dfrac{\text{peak\_velocity}\{PDS_i\}}{\text{peak\_velocity}\{PDS_j\}}$ |
| $\text{max\_slope}\{PDS_i\} = \max\left\{\dfrac{d}{dt}(\text{envelope}\{PDS_i\})\right\}$ |
| $\text{VTI}\{PDS_i\} = \Delta t \cdot \sum_{PDS_i} \text{envelope}\{PDS_i\}$ |
| $\text{ADPV}\{PDS_i\} = \dfrac{1}{t2-t1+1} \sum_{PDS_i=t1}^{t2} \text{envelope}\{PDS_i\}$ |
| $\text{std\_peak\_velocity}\{PDS_i\} = \text{std}(\text{peak\_velocity}\{PDS_{\text{orig}\_i}\})_{(PDS_{\text{orig}\_i}) \in \text{cycles\_before\_averaging}}$ |
| $\text{Mean\_weighted\_V} = \dfrac{\sum_{t=t1}^{t2} \sum_{v=0}^{\text{envelope}(t)} (P_{(t,v)} \cdot v)}{\sum_{t=t1}^{t2} \sum_{v=0}^{\text{envelope}(t)} P_{(t,v)}}$ |

| Velocity Features: |
|---|
| $\text{MMWVC} = \dfrac{\Delta t \cdot \sum_{t=t1}^{t2} \left( \dfrac{\sum_{v=0}^{\text{envelope}(t)} (P_{(t,v)} \cdot v)}{\sum_{v=0}^{\text{envelope}(t)} P_{(t,v)}} \right)}{t2-t1+1}$ |

| Power Features: |
|---|
| $\text{Mean\_power} = \text{mean}\{P_{(t,v)}\}_{(t,v) \in PDS\_i}$ |
| $\text{Max\_power} = \max\{P_{(t,v)}\}_{(t,v) \in PDS\_i}$ |
| $\text{Median\_power} = \text{median}\{P_{(t,v)}\}_{(t,v) \in PDS\_i}$ |
| $\text{std\_power\_flow} = \text{std}\{P_{(t,v)}\}_{(t,v) \in PDS\_i}$ |
| $\text{std\_power\_flow\_dB} = \text{std}\{10 \cdot \log_{10}(P_{(t,v)} + 1)\}_{(t,v) \in PDS\_i}$ |
| $\text{PVTI} = \Delta v \cdot \Delta t \cdot \sum_{t=t1}^{t2} \sum_{v=0}^{\text{envelope}(t)} (P_{(t,v)} \cdot v)$ |
| $\text{total\_power} = \Delta v \cdot \Delta t \cdot \sum_{t=t1}^{t2} \sum_{v=0}^{\text{envelope}(t)} P_{(t,v)}$ |

| Time Features: |
|---|
| $\text{PDS\_duration} = \{t_{end} - t_{start}\}_{(t) \in PDS\_i}$ |
| $\text{PDS\_ECG\_syncronization} = \text{abs}(t(\max\_velocity\{PDS_i\}) - t(\max(R/T - \text{wave})))_{(t,v) \in ROI}$ |
| $\text{duration\_percentage} = \left( \dfrac{\text{PDS\_duration}}{(t_{end} - t_{start})_{(t) \in \text{averaged\_cycle}}} \right)_{(t,v) \in ROI}$ |

| Other Features |
|---|
| Age |
| Weight |
| Sex |
| Height |

Using these parameters, the learning and classifying steps may be implemented as described in the '828 application.

CONCLUSION

The Doppler signatures of the following of tissues and structures may change with pathology: pulmonary emphysema, pulmonary emboli, pulmonary hypertension, pulmonary blood vessel stenosis & malformations, conditions associated with pulmonary fibrosis, pneumonia, atelectasis, pneumothorax, congestive heart failure, pulmonary solid tumors, various cardiac malfunctions that are manifested in the pulmonary blood vessels, tumors, and foreign bodies, etc. Thus, the lung Doppler signals picked up using TPD may be used to provide insights and potentially valuable diagnostic information regarding the structure and integrity of the lung parenchyma and vasculature. TPD may therefore serve as a new non-invasive and non-destructive tool for diagnosis of pulmonary disease & function. It may also enable continuous monitoring of the status of a failing pulmonary or cardiovascular system, and help determine the efficacy and so enable dose calibration, for optimal treatment.

An additional unique diagnostic capability of the TPD is to determine the compliance (elastance) of the pulmonary vascular tree components that changes in cases of arteriosclerosis and other vascular conditions. Vascular compliance can be measured on the basis of the pulse propagation velocity in the vessel because the more rigid the vessel is, the faster the propagation will be. In the case of the lungs, the propagation velocity can be determined from the delay between the time of appearance of any of the lung signals (or their peak, etc.), at different locations along the propagation pathway. Such delay measurements can be made, manually or automatically by appropriate software, in the different records obtained at different lung locations or at different depths beneath a single location.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of determining a breathing rate of a patient comprising the steps of:
    obtaining, using an ultrasound probe that is aimed at the patient's lung, Doppler ultrasound power and velocity data by detecting Doppler shifts of reflected ultrasound induced by moving borders between (1) blood vessels/soft tissue in the lung and (2) air filled alveoli that surround the blood vessels for a period of time that corresponds to a plurality of cardiac cycles~wherein movement of the borders is caused by pressure waves in the blood vessels that result in changes in diameter of those blood vessels in response to blood being pumped through the vessels by a beating heart;
    processing the power and velocity data obtained in the obtaining step using a noise reduction algorithm designed to increase signal from the moving borders with respect to other reflected ultrasound signals;
    extracting an envelope of the power and velocity data with respect to time, wherein at least one parameter used in the envelope extracting step is selected to track variations that correspond to an expected breathing cycle;
    identifying a periodic feature of the envelope extracted in the extracting step;
    determining timing of the periodic feature identified in the identifying step; and outputting an indication of the breathing rate based on the timing determined in the determining step.

2. The method of claim 1, wherein the at least one parameter is configured to pass frequencies less than 0.25 Hz and attenuate frequencies greater than 1.5 Hz.

3. The method of claim 1 wherein, in the obtaining step, the ultrasound probe is operated at a pulse repetition frequency between 1 and 2 kHz.

4. An apparatus for determining a breathing rate of a patient comprising:
    an ultrasound-frequency signal generator configured to drive an ultrasound transducer;
    a receiver configured to receive ultrasound-frequency return signals reflected from a target region in the patient's lungs and detect Doppler shifts of the return signals induced by moving borders between (1) blood vessels/soft tissue in the lung and (2) air filled alveoli that surround the blood vessels, wherein movement of the borders is caused by pressure waves in the blood vessels that result in changes in diameter of those blood vessels in response to blood being pumped through the vessels by a beating heart; and
    a processor configured to (a) process the detected Doppler shifts using a noise reduction algorithm designed to increase signal from the moving borders with respect to other reflected ultrasound signals and output processed power and velocity data for a period of time that corresponds to a plurality of cardiac cycles, (b) extract an envelope of the power and velocity data with respect to time, wherein at least one parameter used for the envelope extraction is selected to track variations that correspond to an expected breathing cycle, (c) identify a periodic feature of the extracted envelope, (d) determine timing of the identified periodic feature, and (e) output an indication of the breathing rate based on the determined timing.

5. The apparatus of claim 4, wherein the at least one parameter is configured to pass frequencies less than 0.25 Hz and attenuate frequencies greater than 1.5 Hz.

6. The apparatus of claim 4, further comprising an ultrasound probe that includes the ultrasound transducer.

7. The apparatus of claim 6, wherein the ultrasound probe is coin-shaped.

8. The apparatus of claim 4 wherein the ultrasound-frequency signal generator operates at a pulse repetition frequency between 1 and 2 kHz.

9. A method of monitoring a patient's heart, the method comprising the steps of:
    obtaining, using an ultrasound probe that is aimed at the patient's lung, Doppler ultrasound power and velocity data by detecting Doppler shifts of reflected ultrasound induced by moving borders between (1) blood vessels/soft tissue in the lung and (2) air filled alveoli that surround the blood vessels for a period of time that corresponds to a plurality of cardiac cycles~wherein movement of the borders is caused by pressure waves in the blood vessels that result in changes in diameter of those blood vessels in response to blood being pumped through the vessels by a beating heart;
    processing the power and velocity data obtained in the obtaining step using a noise reduction algorithm designed to increase signal from the moving borders with respect to other reflected ultrasound signals;
    identifying features in the power and velocity data that occur once per cardiac cycle; and
    determining timing between the identified features.

10. The method of claim 9, wherein the features identified in the identifying step comprise at least one of (a) a feature that corresponds to systolic ventricular contraction, (b) a feature that corresponds to ventricular relaxation, (c) a feature that corresponds to a diastolic rapid filling phase, (d) a feature that corresponds to diastasis, and (e) a feature that corresponds to atrial contraction.

11. The method of claim 9, wherein the features identified in the identifying step comprise features that correspond to systolic ventricular contractions.

12. The method of claim 9, further comprising the step of outputting an indication of how fast the patient's heart is beating based on the timing determined in the determining step.

13. The method of claim 12, wherein the features identified in the identifying step comprise features that correspond to systolic ventricular contractions.

14. The method of claim 9, further comprising the steps of:
predicting a time when a particular feature is expected based on past occurrences of identified features;
detecting a presence of the particular feature at a time that was not predicted in the predicting step; and
outputting an indication that the particular feature was detected at an unpredicted time.

15. The method of claim 14, wherein the features identified in the identifying step comprise features that correspond to systolic ventricular contractions.

16. The method of claim 9 wherein, in the obtaining step, the ultrasound probe is operated at a pulse repetition frequency between 1 and 2 kHz.

17. An apparatus for monitoring a patient's heart comprising:
an ultrasound-frequency signal generator configured to drive an ultrasound transducer;
a receiver configured to receive ultrasound-frequency return signals reflected from a target region in the patient's lungs and detect Doppler shifts of the return signals induced by moving borders between (1) blood vessels/soft tissue in the lung and (2) air filled alveoli that surround the blood vessels, wherein movement of the borders is caused by pressure waves in the blood vessels that result in changes in diameter of those blood vessels in response to blood being pumped through the vessels by a beating heart; and
a processor configured to (a) process the detected Doppler shifts using a noise reduction algorithm designed to increase signal from the moving borders with respect to other reflected ultrasound signals and output processed power and velocity data for a period of time that corresponds to a plurality of cardiac cycles, (b) identify features in the power and velocity data that occur once per cardiac cycle, and (c) determine timing between the identified features.

18. The apparatus of claim 17, wherein the identified features comprise at least one of (a) a feature that corresponds to systolic ventricular contraction, (b) a feature that corresponds to ventricular relaxation, (c) a feature that corresponds to a diastolic rapid filling phase, (d) a feature that corresponds to diastasis, and (e) a feature that corresponds to atrial contraction.

19. The apparatus of claim 17, wherein the identified features comprise features that correspond to systolic ventricular contractions.

20. The apparatus of claim 17, wherein the processor is further configured output an indication of how fast the patient's heart is beating based on the determined timing.

21. The apparatus of claim 20, wherein the identified features comprise features that correspond to systolic ventricular contractions.

22. The apparatus of claim 17, wherein the processor is further configured to predict a time when a particular feature is expected based on past occurrences of identified features, detect a presence of the particular feature at a time that was not predicted, and output an indication that the particular feature was detected at an unpredicted time.

23. The apparatus of claim 22, wherein the identified features comprise features that correspond to systolic ventricular contractions.

24. The apparatus of claim 17, further comprising an ultrasound probe that includes the ultrasound transducer.

25. The apparatus of claim 24, wherein the ultrasound probe is coin-shaped.

26. The apparatus of claim 17 wherein the ultrasound-frequency signal generator operates at a pulse repetition frequency between 1 and 2 kHz.

* * * * *